(12) United States Patent
Howie et al.

(10) Patent No.: US 11,690,878 B2
(45) Date of Patent: Jul. 4, 2023

(54) SYNERGISTIC COMPOSITIONS

(71) Applicant: Lintbells Limited, Hertfordshire (GB)

(72) Inventors: John Howie, Hertfordshire (GB); Glen Vile, Hertfordshire (GB)

(73) Assignee: Lintbells Limited, Hertfordshire (GB)

( * ) Notice: Subject to any disclaimer, the term of this patent is extended or adjusted under 35 U.S.C. 154(b) by 46 days.

(21) Appl. No.: 16/748,580

(22) Filed: Jan. 21, 2020

(65) Prior Publication Data

US 2021/0220409 A1 Jul. 22, 2021

(51) Int. Cl.
| | |
|---|---|
| *A61K 35/618* | (2015.01) |
| *A61K 35/60* | (2006.01) |
| *A23L 33/125* | (2016.01) |
| *A23L 33/12* | (2016.01) |
| *A61K 47/26* | (2006.01) |

(52) U.S. Cl.
CPC .......... *A61K 35/618* (2013.01); *A23L 33/12* (2016.08); *A23L 33/125* (2016.08); *A61K 35/60* (2013.01); *A61K 47/26* (2013.01)

(58) Field of Classification Search
None
See application file for complete search history.

(56) References Cited

U.S. PATENT DOCUMENTS

| 10,278,995 B1 | 5/2019 | Van Kampen et al. |
|---|---|---|
| 2006/0039992 A1 | 2/2006 | Miller, Jr. et al. |

FOREIGN PATENT DOCUMENTS

| AU | 2019100451 A4 | 5/2019 |
|---|---|---|
| CN | 109984251 A | 7/2019 |
| EP | 1146870 B1 | 10/2001 |
| EP | 1378243 A1 | 1/2004 |
| WO | 1998/07326 A1 | 2/1998 |
| WO | 0056164 A1 | 9/2000 |
| WO | 2004075653 A1 | 9/2004 |
| WO | 2006004438 A1 | 1/2006 |
| WO | 2008153426 A1 | 12/2008 |

OTHER PUBLICATIONS

Bettjeman et al. (2018) J. Amer. Oil Chem. Soc. vol. 95(7): 779-786. (Year: 2018).*
Cobb et al. (2006) Clin. Rheumatol. 25: 275-284. (Year: 2006).*
Coulson et al. (2019) In: Progress in Drug Research, vol. 70: p. 91-132. (Year: 2019).*
James et al. (1997) Rheumatoid Arthritis, 27: 85-97. (Year: 1997).*
Tallarida (2011) Genes and Cancer, 2(11): 1003-1008. (Year: 2011).*
E.G. Bligh et al., "A Rapid Method of Total Lipid Extraction and Purification," Can. J. Biochem. Physiol. 1959 37(8), pp. 911-917.

* cited by examiner

*Primary Examiner* — Russell G Fiebig
(74) *Attorney, Agent, or Firm* — McCarter & English, LLP; Yu Lu

(57) ABSTRACT

The invention concerns novel compositions, comprises at least 2 different sources of ω-3 fatty acids, wherein the first is hoki roe powder at 5% (w/w) particularly for use in supplements and/or animal or human food stuffs. The invention may further relate to the treatment of veterinary conditions, such as use in the improvement of inflammation or joint related disorders that maybe associated with inflammation.

12 Claims, 4 Drawing Sheets

SYNERGISTIC COMPOSITIONS

TECHNICAL FIELD

The invention concerns novel compositions comprising a combination of two different blended marine-sources including at least two powder components including least hoki roe (HR) powder and preferably green-lipped mussel (GLM) powder. The invention further extends to the use of that composition in human and veterinary applications, particularly in supplements or nutraceuticals thereby providing nutritional support in joint health.

BACKGROUND

Nutraceuticals, food and health supplements are often utilised to improve or support joint structure and maintain joint mobility in mammals, including humans and animals.

The biological inflammatory pathway is directly linked with joint health including, for example, joint mobility. Potentially, lipids including pro-resolving lipid mediators, bioactive peptides may also have a role but may act via different pathways.

An effect has been shown to be derived from essential fatty acids (EFAs). Several enzymes implicated in the biological inflammatory pathway are thought to be impacted by the presence or absence of these EFAs and is also dependent of the type of EFA.

A significant level of omega ($\omega$) polyunsaturated fatty acids, particularly $\omega$-3, is likely to support the body's natural anti-inflammatory process and may therefore be useful. In particular, these particular EFAs are metabolised into anti-inflammatory eicosanoids. The presence of $\omega$-3 bolsters the existing anti-inflammatory pathway because they will be preferentially acted upon in the process but in their in their absence the natural substrate, including other EFAs such as arachidonic acid, would metabolise to generate pro-inflammatory agents.

Although GLM powder can be utilised for the purpose of providing a source $\omega$-3 within supplement compositions, the quality and content of the $\omega$-3 fatty acid is not always reliable and may not always be sufficient for products intended for maintaining joint health in humans or animals.

However, it remains desirable to provide effective compositions for use in supporting joint health, whether as a long term maintenance product, e.g. in food stuffs or supplements, or as a short term dietary solution. In particular, the ability to provide high specification sources of GLM powders that correlate with desired technical specification that sufficient to meet these applications is increasing challenging. The invention therefore comes about from the continued need to provide new compositions useful in the aforementioned commercial applications.

SUMMARY OF INVENTION

The invention concerns a composition comprising a combination of two powder components including at least green-lipped mussel (GLM) powder; and at least 5% (w/w) hoki roe (HR) powder.

The invention extends to a composition comprising: a blend of at least two different powder components each comprising $\omega$-3 fatty acids, wherein a first of those powder components is 5% (w/w) or more hoki roe (HR) powder and a combination of the powder components together provide at least 3.3% $\omega$-3 fatty acids. Preferably, a second of the two powder components is green lipped mussel powder.

In the first instance, the applicant made the observation that when providing a composition for the before-described application, the selection of the $\omega$-3 fatty acid source is very important. The $\omega$-3 fatty acids in any given powder source on the market varies considerably. The applicant's preliminary investigations confirmed that some GLM powder specifications did not provide enough $\omega$-3 to meet the technical criteria for the intended purpose, as compared to a higher specification product which is rare and less easily available to the market.

However, GLM remains an important base source of $\omega$-3 fatty acids, even when low and the inventors further investigated other ways in which GLM-based compositions would nonetheless provide a solution. In doing so it was determined that including a minimum amount of a different, specifically selected, $\omega$-3 fatty acid source, in combination with the lower specification GLM powder, raised the $\omega$-3 content to an acceptable level. It was elucidated through testing that using at least 5% of Hoki Roe powder, blended with the lower specification GLM powder achieved this solution.

It was further elucidated through in vitro assay testing that an unexpected, enhanced level of inhibitory activity can be observed in a composition by introducing a particular selection or combining sources of $\omega$-3 content. Such inhibitory activity is highly relevant to supporting the inflammatory response pathway and maintaining optimum joint health. The anti-inflammatory activity of a blend of hoki roe powder and green lipped mussel powder is preferably measured as a co-efficient of between 0.05 and 0.25, determined according to the methods described herein below.

The in vitro inhibition activity observed by the applicant is considered to be far greater than the mere additive effect that would be expected from the omega 3 EFA levels combination alone. Therefore, the applicant has determined a most unexpected synergistic effect can be achieved by the invention. That is, the specific introduction of hoki roe at a de minimus level and/or further a specific selection of this powder component with a lower specification GLM extract maintains a higher level of competitive enzyme activity than would be expected based purely on omega 3 EFA content. In embodiments, the invention therefore concerns a food product, supplement or nutraceutical comprising the composition having the components as recited in the claims and as described herein.

Such a composition would meet or exceed the technical criteria required, in terms of content and/or activity and thus enable consistent and improved efficacy of a GLM-based product for the purpose of supporting joint health. The invention is useful in the provisions of a food stuff or supplement comprising the composition as described herein. The food stuff or supplement may further comprise one or more useful excipients desirable to make the supplement more palatable, or may provide other benefits. The excipient may include one or more of the following excipients including but not limited to: Glucosamine, Hyaluronic Acid and Chondroitin Sulphate.

In preferred embodiments of either aspect of the invention the hoki roe powder is in the range from 5% to 95% (w/w) of the total composition mass. In embodiments, the hoki roe powder comprises a total fat content of 14% to 40% but importantly may comprise a total omega-3 fatty acid content from 2% to 20%.

As regards the green-lipped mussel content, the green-lipped mussel powder comprises a total fat content from 7% to 13%. It is envisaged that in embodiments the green-lipped mussel powder comprises a total ω-3 fatty acid content in the range of 2% to 7% ideally 2.0% to 5.0%.

The composition of the invention is particularly useful as a supplement for humans or a veterinary product and may be used to prevent inflammation, to maintain low levels of inflammation and or to treat inflammation. The composition, food stuff or supplement may be for use in the treatment and/or maintenance of joint health of a human or animal. Further, the treatment and/or maintenance involves support of anti-inflammatory pathways in the human or animal.

The invention further extends to a method of maintaining joint health comprising administering to a animal in need thereof the composition disclosed herein. In embodiments the maintenance of health involves supporting anti-inflammatory pathways of the animal including the prevention of inflammation.

DETAILED DESCRIPTION

GLM is used to provide EFAs into the body. They support the anti-inflammatory process by being preferentially acted upon in the anti-inflammatory system, resulting in anti-inflammatory mediators. In the absence of these omega 3 EFAs, other EFAs, notably arachidonic acid, will be used as substrates, resulting in pro-inflammatory mediators.

Figure 1:
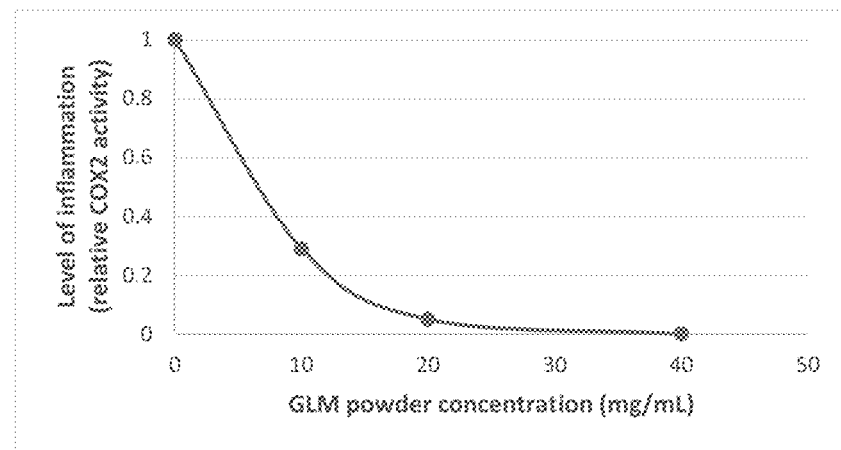
FIG. 1 is a graph illustrating a dose response curve for gold standard GLM.

A dose response is seen in effect depending upon the quantity of GLM used i.e. as the concentration is increased the activity of an inflammatory process (COX2 activity) drops away—see FIG. 1.

Figure 2:
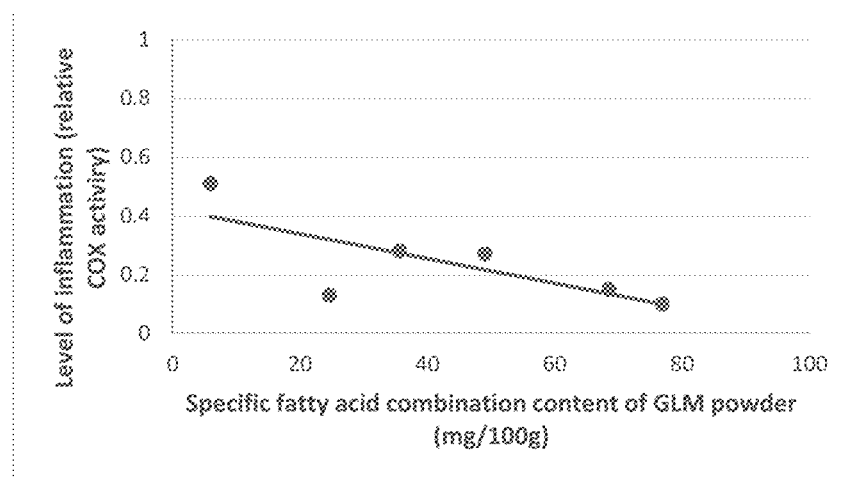
FIG. 2 is a graph illustrating the varying GLM quality sample work.

The inventors have identified that when GLM is utilised at the same concentration but with a lower EFA specification, a decreased effect on an inflammatory process is seen—see FIG. 2.

Figure 3:
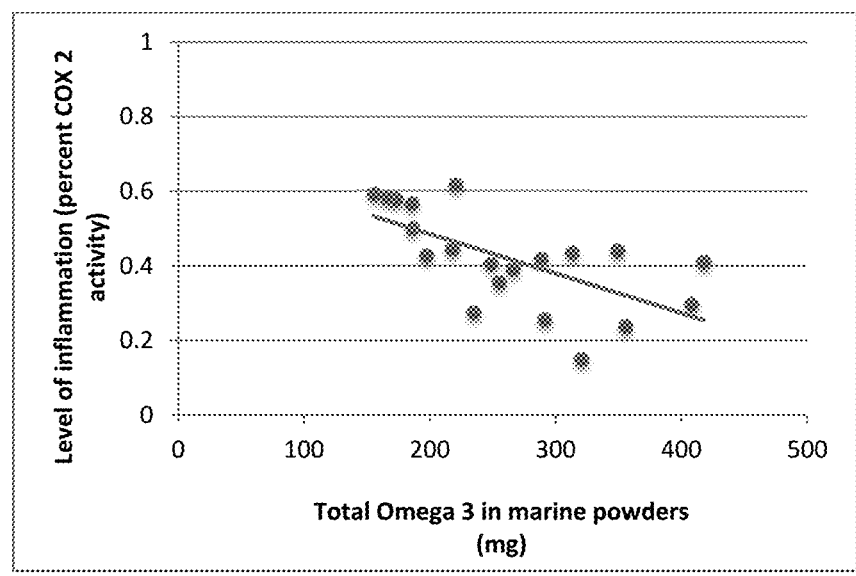
FIG. 3 is a graph illustrating the Omega 3/cox-2 ratio data.

Further the inventors have identified a correlation between Omega 3 EFAs and activity of an inflammatory process i.e. with increasing EFAs activity of an inflammatory process decreases—see FIG. 3.

Figure 4:
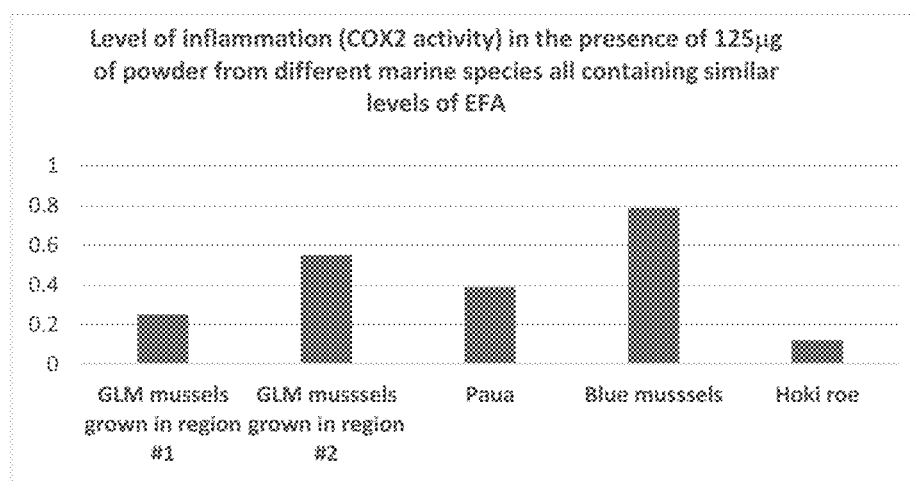
FIG. 4 is a graph illustrating marine samples screening work comparing GLM, Paua, Blue mussels and Hoki roe.

It has further been identified that certain marine species are more effective at decreasing levels of an inflammatory process despite having similar levels of total EFA, suggesting the bioactivity is down to certain EFAs over others—see FIG. 4.

Hoki roe has been identified as one source that appears to have higher profiles of certain EFAs that is similar to GLM in some EFAs. The potential to utilise Hoki as a replacement/top up for reduced EFA spec GLM & reduced concentration of full spec GLM was investigated.

Figure 5:
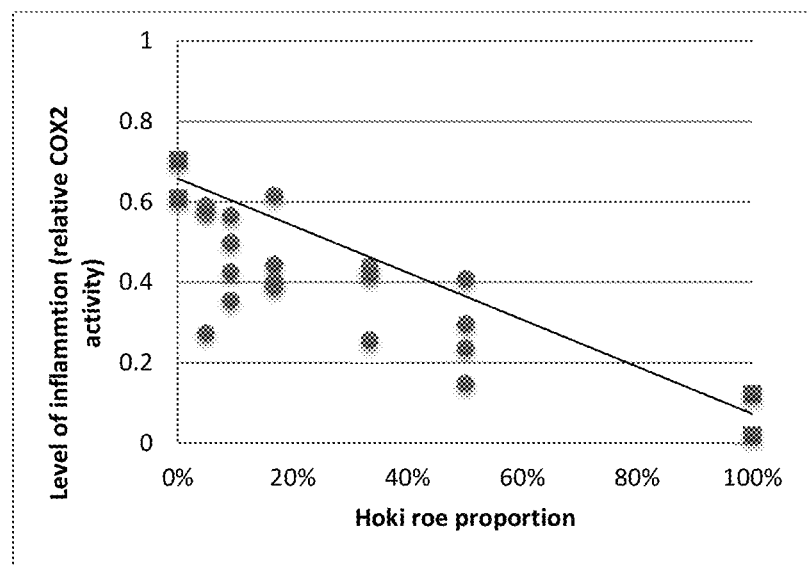
FIG. 5 is a graph illustrating the effects at specific % combinations showing the predicted effect on inflammatory processes and the actual effect.
Figure 6:
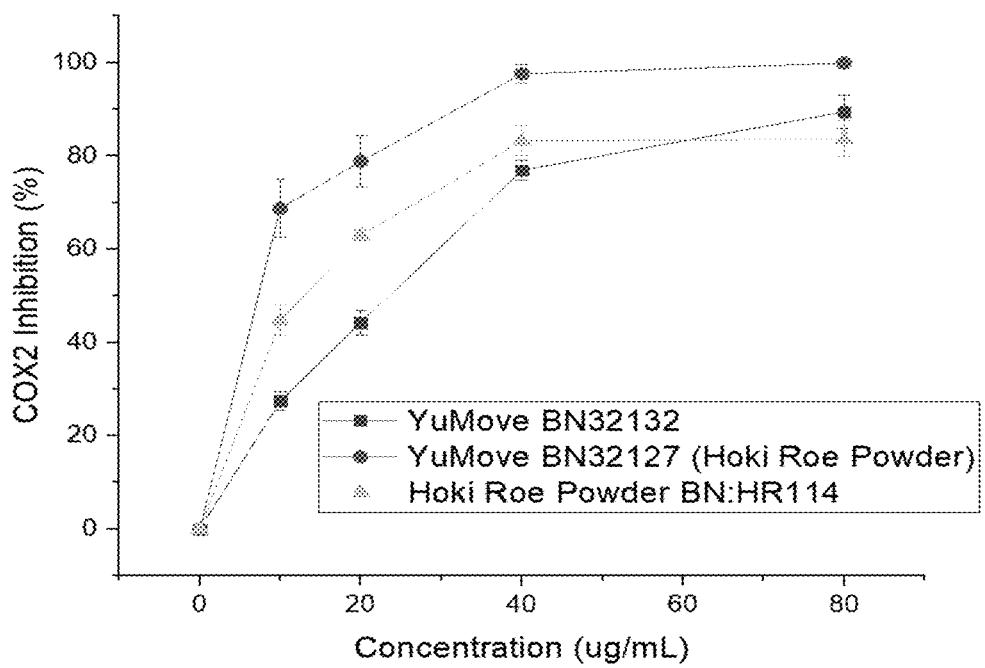
FIG. 6 is a graph illustrating the concentration-dependent inhibition of COX2 of the 3 different sampled powders.
Figure 7:
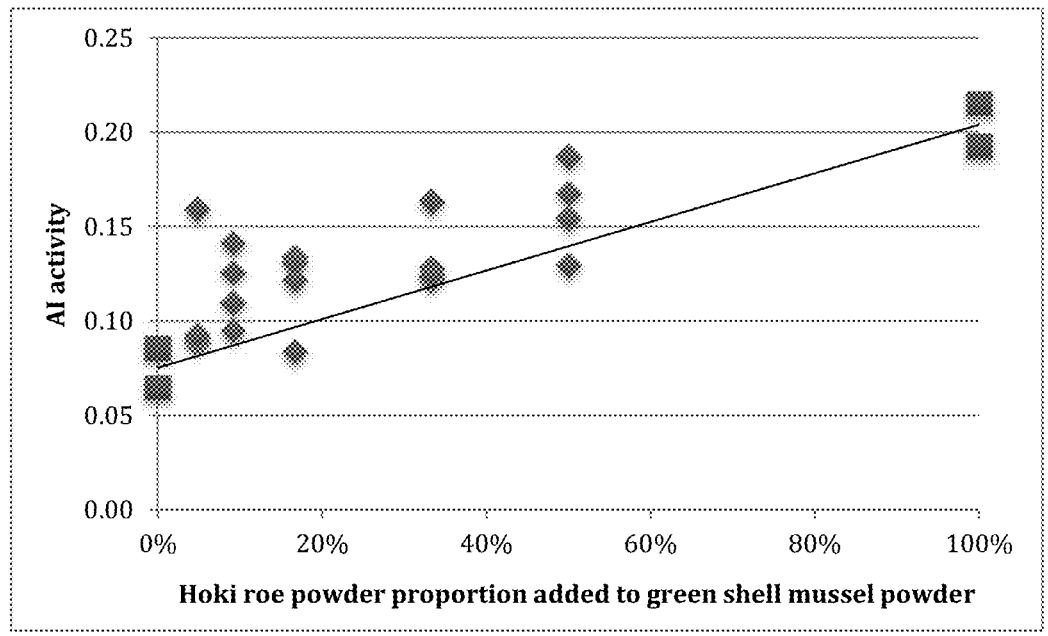
FIG. 7 is a graph illustrating anti-inflammatory activity exhibited vs % powder blend and compared with the H powder and X powder expected trend line.
Figure 8:
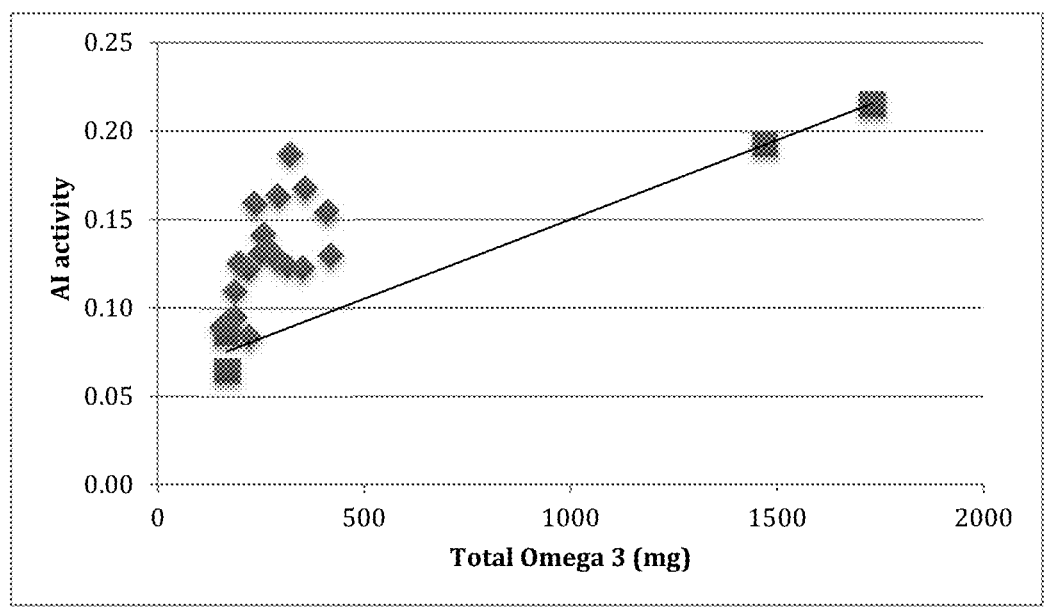
FIG. 8 is a graph illustrating the anti-inflammatory activity of x+H blends as compared to the levels of total Omega-3 fatty acids as compared to H powder and X powder expected trend line.

Based on the relative effects of GLM & Hoki on an inflammatory process, a number of combinations were tested of reduced concentration GLM/Hoki added or reduced EFA GLM/Hoki added. The expected additive effect was calculated based on the inflammatory performance of the original GLM & Hoki samples, with the aim to maintain the effect expected from a full concentration, full spec GLM—see FIG. 5.

In fact, what the inventors identified is a greater effect on the inflammatory processes in the combination that would be expected from sum of parts. The invention demonstrates a synergistic effect that can be used to maintain a better level of support for the anti-inflammatory system.

EFAs are thought to be important as a component in any composition which is intended to help support natural anti-inflammatory processes related to human or animal joints, as described here before.

In particular ω-3 EFAs appear to act as dual competitors of arachidonic acid oxygenation by both the cyclooxygenase (COX) and lipoxygenase (LOX) pathway and thus are useful in said applications.

EFA and ω-3 fatty acids particularly can be found in the green-lipped mussel (GLM) or green shell mussel (GSM; *Perna canaliculus*). As described previously, alternatives or additives were sought for investigation due to the variation in the specification of GLM powders and the fact that alone, many existing powder sources of GLM did not necessarily provide a specification with a sufficient content of ω-3 fatty acids.

A variety of marine sources were reviewed as potential sources of desirable ω-3 fatty acid components. Generally marine-derived high ω-3 fatty acid sources are oils from shellfish or fish organs.

A range of these types of oils were screened as potential substitutes for part of a composition comprising GLM in order to improve the total ω-3 fatty acid content. While being good sources of ω-3 fatty acids it was found that it was difficult to blend the oils with the GLM powder to provide a homogenous powder suitable for formulation into applicable products.

However, one such source of ω-3 fatty acids was the dried roe powder from *Macruronus novaezelandiae*, or the white fish hoki. Thus hoki roe powder was tested to determine whether its addition to the GLM powder would improve the content of the EFA, particularly the ω-3 fatty acids.

The suitability of NZ hoki roe powder was determined by measuring the levels of the ω-3 fatty acids in the green lipped mussel powder before addition of hoki roe powder, then after addition, to examine if the ω-3 levels were elevated to the required specification by the combination. The required specification was provided by a GLM powder known to give a commercially desired therapeutic outcome, with a comparatively high ω-3 fatty acid specification.

To ensure that the novel blend of powders also exhibited desired anti-inflammatory activity (despite the inclusion of lower ω-3 content GLM) in vitro-enzyme activity was tested and compared to a standard desirable specification product, as used by the applicants.

A commonly used in vitro process of measuring of anti-inflammatory activity was used, namely by determining the level of in vitro competition of the COX2 enzyme, which is known to be a pathway involved significantly in the inflammation process, discussed herein before.

Methods

New Zealand green lipped mussel powder and New Zealand hoki roe powder were obtained from commercial sources and lipid extracts were obtained from the individual powders, or blends of the powders, using the Bligh and Dyer method. This method is described in the following published reference concerning the same (Bligh and Dyer, A rapid method of total lipid extraction and purification. Canadian Journal of Biochemistry and Physiology 1959, 37: 911-917). The fatty acid components of the lipid extracts were measured using AOAC method 963.22.

Results

A first set of data was generated by measuring and comparing the amount of ω-3 fatty acids in a standard reference source of GLM product (X) known by the applicant to have an acceptable specification and thus the required amount of ω-3 fatty acid suitable and desirable for use. A further source of GLM powder (x) known to be of a lower specification was also measured.

The GLM x powder, alone, presented insufficiently, measuring at significantly less ω-3 fatty acid than the reference powder GLM (X) with low COX2 activity and was thus below the required specification required for the commercially desirable applications.

A new combination was tested to determine how ω-3 fatty acid levels were impacted when the below spec product x was supplemented with an amount of a different powder known to be rich in ω-3.

Hoki roe powder (H) had previously been selected from a variety of sources, on the basis that it had good potential for elevating the total ω-3 fatty acid content and is able to be easily blended into the GLM powder.

In order to establish if a lower specification GLM powder could be raised to the required specification by addition of hoki roe powder it was theoretically determined that at least 5%, preferably 8% of a specific hoki roe powder (BN: HR114) added to a lower specification GLM powder (x) would raise the total ω-3 content score (the measure of % fatty acid in the total fat of the product) to a level that meets the required specification.

It was determined by measurement that by including 8% hoki roe powder (H) into a blend with the below specification GLM powder (x), the ω-3 fatty acid content was increased to 3.5%, very close to the level shown for the standard powder X (BN32132) as in the Table 1 below:

TABLE 1

| Composition | Batch number | GLM powder component (g) | H powder component (g) | Total ω-3 score (g/100 g) |
|---|---|---|---|---|
| GLM powder-below spec (x) | | 100 | 0 | 3.1 |
| Hoki roe powder (H) | BN:HR114 | 0 | 100 | 5.1 |
| GLM powder-below spec plus H (x + H) | | 95 | 5 | 3.3 |
| GLM powder-below spec plus H (x + H) | BN32127 | 92 | 8 | 3.5 |
| GLM powder-Lintbell standard spec (X) | BN32132 | 100 | 0 | 3.6 |

Biological Activity

Different quality specifications of GLM (that varied in the levels of ω-3 fatty acids) were combined with Hoki Roe powder in different ratios. We then measured total ω-3 fatty acids in the combination product and the COX inhibitory scores of those powders compared to the source GLM (x) and Hoki powders (H).

Next, anti-inflammatory activity of the above examples was measured to determine the likely potential for biological impact of the combination as compared to the expected activity based on the new combinations of sourced ω-3 fatty acids.

The COX2 inhibition was determined by incubating lipid extracts of the powder blend combinations with commercially available mammalian COX2 enzyme and the enzyme's activity was measured as the co-oxidation of N,N,N',N'-tetramethyl-p-phenylenediamine (TMPD) by PGG2 to produce oxidised TMPD, which is blue in colour and readily detectable at 611 nm.

The COX2 inhibitory activity of the powder blend combinations was determined from the lipid extract concentration-dependent inhibition of the COX2 enzyme, or by the anti-inflammatory activity (AI) score of the powder sample, calculated as the inverse of the concentration of lipid extract required to inhibit the COX2 enzyme by 50% ($IC_{50}$) multiplied by the total weight of lipid extracted from the powder blend combinations.

As can be seen in FIG. 1, it was determined that concentration-dependent inhibition of COX2 by the below specification GLM powder (x) blended with 8% Hoki roe powder (H) to produce x+H (BN32127) powder was significantly greater than a green lipped mussel powder X (BN 32132) alone, which had displayed a similar ω-3 fatty acid level (as was shown in Table 1) and thus would have been assumed to be similar.

Rather surprisingly, the concentration-dependent inhibition of COX2 by x+H (BN 32127) was even greater than a 100% hoki roe powder H (BN:HR114), which exhibited an ω-3 level that was significantly greater than x+H, as shown in Table 1.

As can be seen in FIG. 2, it was further established that anti-inflammatory activity exhibited by x+H at various percentage of % H blend (diamond data points) was greater than would be expected from the activity one would expect when plotting a linear trend line showing activity of the GLM powder X (far left square data points) and Hoki roe powder H alone (far right square data points). The linear trend line between the two indicates what might be expected from a simple additive effect of the two powders suggesting the two have an enhanced effect that in combination goes far beyond the simple addition of the individual effect.

This trend was further observed since the anti-inflammatory activity of x+H at various % powder blends (diamond data points) was also greater than would be expected from: the levels of total Omega-3 fatty acids in the H and X alone as shown in FIG. 3 where the large square data points display the linear trend line relationship indicating what would be expected from a simple additive effect achieved by combining the powders. The blended powder exceeded the expected activity quite significantly, indicating the novel combination provides for an enhanced and thus synergistic rather than a mere accumulative effect.

The invention claimed is:

1. A composition comprising a combination of two powder components, wherein the combination consists of:
    (1) green-lipped mussel (GLM) powder; and
    (2) at least 5% and up to about 50% (w/w) hoki roe (HR) powder,
    wherein the composition synergistically inhibits COX2 activity.

2. The composition of claim 1, wherein the hoki roe powder is present in about 5% or about 10% (w/w) of the total composition.

3. The composition of claim 1, wherein the green-lipped mussel powder comprises a total fat content from 7% to 13%.

4. The composition of claim 1, wherein the green-lipped mussel powder comprises a total ω-3 fatty acid content in a range of 2.0% to 5.0%.

5. The composition of claim 1, wherein the hoki roe powder comprises a total fat content of 14% to 40%.

6. The composition of claim 1, wherein the hoki roe powder comprises a total ω-3 fatty acid content from 2% to 20%.

7. A food stuff, nutraceutical, or supplement comprising the composition of claim 1.

8. The food stuff, nutraceutical, or supplement of claim 7, further comprising at least one excipient chosen from glucosamine or hyaluronic acid.

9. A method of treating a subject, the method comprising administering to the subject the composition of claim 1, wherein the subject is a human or a non-human animal.

10. The method of claim 9, wherein the method treats inflammation or maintains low levels of inflammation in the subject, wherein the subject is the non-human animal.

11. The method of claim 9, wherein the method maintains health of the subject.

12. The method of claim 9, wherein the method maintains joint health of the subject.

* * * * *